United States Patent [19]

Marks et al.

[11] Patent Number: 5,345,032

[45] Date of Patent: Sep. 6, 1994

[54] USE OF METAL CHELATE COMPLEXES IN DEHALOGENATION

[75] Inventors: Trevor S. Marks; Andrew Maule, both of Wiltshire, England

[73] Assignee: The Public Health Laboratory Service Board, London, England

[21] Appl. No.: 47,837

[22] Filed: Apr. 19, 1993

Related U.S. Application Data

[63] Continuation of Ser. No. 634,874, Jan. 8, 1991, abandoned.

[30] Foreign Application Priority Data

May 9, 1988 [GB] United Kingdom ............... 8810944.2
May 9, 1989 [GB] United Kingdom ............... 8905423.3

[51] Int. Cl.$^5$ ........................ C07C 17/24; C07C 9/04; A62D 3/00
[52] U.S. Cl. ............................. 588/207; 540/139; 540/145; 570/205; 570/230; 585/733; 588/206; 422/129
[58] Field of Search ............... 570/205, 230; 540/139, 540/145; 585/733; 588/206, 207

[56] References Cited

U.S. PATENT DOCUMENTS

| | | | |
|---|---|---|---|
| 2,867,626 | 1/1959 | Erdman et al. | 260/314 |
| 3,004,985 | 10/1961 | Obika et al. | 260/314 |
| 3,072,539 | 1/1963 | Fancher et al. | 195/103.5 |
| 3,252,892 | 5/1966 | Gleim | 208/206 |
| 3,687,863 | 8/1972 | Wacher | 540/145 |
| 3,693,327 | 9/1972 | Scheinberg | 540/145 |
| 4,234,455 | 11/1980 | Homeier et al. | 252/430 |
| 4,372,893 | 2/1983 | Eckert | 260/465 SE |
| 4,619,923 | 10/1986 | Kappar et al. | 514/185 |
| 4,784,736 | 11/1988 | Lonsdale et al. | 540/139 |
| 4,885,114 | 12/1989 | Gordon et al. | 540/145 |
| 5,004,551 | 4/1991 | Sublette | 210/763 |
| 5,032,291 | 7/1991 | Sublette | 210/757 |
| 5,120,453 | 6/1992 | Frame et al. | 210/759 |

FOREIGN PATENT DOCUMENTS

8910772 11/1989 World Int. Prop. O. .......... 588/206

OTHER PUBLICATIONS

Tachkova et al, "Chem. Abstracts," 90(15) 121787d (1979).
Schravzer et al, "Chem. Abstracts" 90(11) 820625 (1979).
Berry et al, "Chem. Abstracts" 88(21) 147476k (1978).
Boucher et al, "J. Am. Chem. Soc." 1967, vol. 89, No. 6, pp. 1340–1345.
Fukamachi et al, "Chem. Abstracts" 1987, vol. 107, 135470b.
Stotter, "J. Inorg. Nucl. Chem." 1977, vol. 39, pp. 721–727.
Murakami et al, "J. Am. Chem. Soc." 1980, 102, 6736–6744.
Zanette et al, "J. Org. Chem.," vol. 44, No. 13 1979, 2308–2309.
Klecka et al, "Chemosphere", vol. 13, No. 3, pp. 391–402, 1984.
Inoue et al, "Chemistry Letters", pp. 1157–1160, 1974.

*Primary Examiner*—Joseph E. Evans
*Attorney, Agent, or Firm*—Nixon & Vanderhye

[57] ABSTRACT

A method for dehalogenation of organohalogen compounds, e.g. environmental pollutants in industrial waste. The organohalogen is reacted with a reducing agent in the presence of a selected metal-centered corrin, porphyrin or phthalocyanine complex. Preferred complexes are hydrolysis products of cyanocobalamin, of formula (I), in which $R^1$ is $NH_2$ or OH, $R^2$ is H, $CH_2CH_2COOH$ or $CH_2CH_2CONH_2$, $R^3$ is H, $CH_2CH_2COOH$ or $CH_2CH_2CONH_2$, and $R^4$ is $NHCH_2CH(OH)CH_3$, OH or $NH_2$. The complex is preferably immobilized on a substrate. Some novel metal-centered porphyrin complexes are also described. A dehalogenation apparatus using the method of the invention is also described.

23 Claims, 1 Drawing Sheet

USE OF METAL CHELATE COMPLEXES IN DEHALOGENATION

This is a continuation of application Ser. No. 07/634,874, filed Jan. 8, 1991, now abandoned.

This invention relates to a method of use of metal chelate complexes, in particular metal complexes of certain porphyrins, corrins and phthalocyanines in the dehalogenation of organo-halogen compounds, especially organohalogen pollutants. The invention also relates to novel metal-porphyrin and metal-corrin complexes, including some such complexes which are suitable for use in this method.

Organohalogen compounds present an environment pollution problem. They may enter soil and aquatic environments by several routes and may threaten the drinking water supply. They are generated in large quantities as wastes by the chemical industry. Disposal of these wastes may be by incineration, which is expensive, or more commonly precipitation followed by landfill dumping which is cheaper but leads to high local concentrations of these pollutants.

An important class of organohalogen compounds are insecticides, which are introduced deliberately and directly into the environment, or else may enter the environment indirectly, for examples as a result of processing sheep fleeces obtained from sheep which have been dipped in solutions of insecticides.

Some examples of organochlorine insecticides are briefly mentioned below.

DDT: 1,1,1-trichloro-2,2-bis(p-chlorophenyl)ethane, (1):

Commercially available DDT often consists of a mixture of (1) with several other organochlorine compounds including: 1,1,1-trichloro-2-(O-chlorophenyl)-2-(p-chlorophenyl)ethane, 1,1-dichloro-2,2-bis(p-chlorophenyl)ethane (DDD or TDE), 1-(p-chlorophenyl)-2,2,2-trichloroethanol, 1,1,1-trichloro-2,2-bis(o-chlorophenyl)ethane and bis(p-chlorophenyl)sulphone. Degradation of commercial DDT may lead to other organochlorine compounds being present.

Lindane: 1,2,3,4,5,6-hexachlorocyclohexane (2):

Commercially available Lindane may contain a number of stereoisomers of (2).

Dieldrin: 1,2,3,4,10,10-hexachloro-6,7-epoxy-1,4,4a,5,6,7,8,8a-octahydro-1,4-endo, endo-5,8-dimethanonaphthalene (3):

Organohalides are often extremely persistent, i.e. they are not easily degraded into environmentally acceptable or biodegradable products. Consequently they may be transmitted along the food chain to the detriment of higher forms of life including man. It is therefore desirable to find cheap and effective methods of degrading organohalides, particularly those which are persistent pollutants.

It is known that certain porphyrins and corrins are effective at causing and/or accelerating the degradation of organohalides by dehalogenation. Porphyrins, corrins and phthalocyanines are large, cyclic, metal-chelating, amines of related structure.

Porphyrins contain the ring system (4):

which may carry peripheral substituents.

A number of porphyrin ring systems exist in nature, for example the protoporphyrin (4A), haematoporphyrin (4B), uroporphyrin (4C) and coproporphyrin (4D) systems:

(4A)

(4B)

(4C)

(4D)

Corrins appear to exist in a number of isomeric forms in which the position of double and single bonds in their 19-membered peripheral ring system may vary, as will be seen in the discussion of structures 5A–5H below. The general abbreviation (5):

(5)

is used herein to represent all forms of the corrin ring including isomeric forms and those carrying peripheral substituents.

Phthalocyanines contain the ring system (6).

(6)

In porphyrin, corrin and phthalocyanine ring systems one or more of the central nitrogen atoms may be bonded to one or more hydrogen atoms, or all 4 may be co-ordinated to a central metal atom, which may itself be additionally complexed with one or more other ligands, for example to form the metal-co-ordinated centre:

where M is a metal atom or ion, and where $L_1$ and $L_2$ if present represent the same or different ligands.

Porphyrins and corrins containing metal centres are known in nature. For example haematin, haem and haemin have protoporphyrin ring systems with an Fe(III)OH, a Fe(II) and a Fe(III) Cl centre respectively. Chlorophyll is a magnesium centred porphyrin ring. Such porphyrins are frequently found as parts of larger biological molecules, for example haemoglobin contains an iron-centred porphyrin complexed with proteins. Examples of known metal-centred corrins include the cobalt centred corrins found in the vitamin B12 series of compounds, e.g. vitamin B12 itself, i.e. cyanocobalamin, also known simply as cobalamin, (5A):

Closely related to cyanocobalamin (5A) is dicyanocobalamin, which has a structure analogous to cyanocobalamin but in which two CN ligands are coordinated to the central cobalt ion and the ribazole residue does not chelate with the cobalt.

Other known centred corrins include hydroxycobalamin, adenosylcobalamin and cobaloximes.

Other known cobalt-centred corrins are those described by Bonnett et al (1971) i.e. Neovitamin B12, a steroisomer of (5A) in which the H and CH2CH2CONH2 substituents at ring position 13 are transposed, and the compounds (5B i–vi) of structure:

i: Cobinamide $R^1=NH_2$, $R^2=H$, $R^3=CH_2CH_2CONH_2$, $R^4=NHCH_2CH(OH)Me$.

ii: Neocobinamide $R^1=NH_2$, $R^2=CH_2CH_2CONH_2$, $R^3=H$, $R^4=NHCH_2CH(OH)Me$.

iii: Cobyric Acid: $R^1=NH_2$, $R^2=R^3=CH_2CH_2CONH_2$, $R^4=OH$.

iv: Neocobyric Acid: $R^1=NH_2$, $R^2=CH_2CH_2CONH_2$, $R^3=H$, $R^4=OH$.

v: Heptamethyl Cobyrinate: $R^1=R^4=OMe$, $R^2=H$, $R^3=CH_2CH_2CO_2Me$.

vi: Heptamethyl Neocobyrinate: $R^1=R^4=OMe$, $R^2=CH_2CH_2CO_2Me$, $R=H$.

Cobalt centred corrins of formula (5C and D) are described by Gossauer et al (1977):

| 5C | R | L |
|---|---|---|
| i | H | CN |
| ii | H | SCN or NCS |
| iii | Br | CN |
| iv | I | CN |
| v | NO2 | CN |
| vi | NH2 | CN |
| vii | NHCOCH3 | CN |

| 5D | R |
|---|---|
| i | H |
| ii | Br |
| iii | I |
| iiv | NO₂ |
| v | NH₂ |
| vi | NH₃⁺ CF₃COO⁻ |
| vii | NHCOCH₃ |

Bormann et al (1967) describes cobalt and nickel centred corrins of formulae 5E, 5F and 5G.

| 5E | R¹ | R² |
|---|---|---|
| i | H | H |
| ii | CN | H |

| 5F | R¹ | R² |
|---|---|---|
| i | H | H |
| ii | CN | H |

Bieganowski and Friedrich (1980) also describe Fe(III) centred analogues of cyanocobalamin (5A) and cobyric acid (5Biii).

Holze and Gossauer (1986) describe various degradation products of cyanocobalamin (5A) including (5H) in which the ribazole residue has been removed:

Some investigations of dehalogenation of organohalides by porphyrins and corrins have been carried out, as briefly reviewed below.

Wade and Castro (1973), Miskus et al (1965) and Zoro et al (1974) describe the dehalogenation of a wide range of organohalides by iron-centered porphyrins such as iron (II) deuteroporphyrin IX, haematin, haemoglobin and haemin. Porphyrins are known to dehalogenate some organohalide insecticides, including DDT, Lindane and Dieldrin. Castro (1964) discusses the possible reaction between iron (II) deuteroporphyrin and DDT, and Wade & Costro (op cit) include DDT and DDD among the organohalides they studied. Stotter (1976) describes reactions between DDT and iron-centred porphyrins such as cytochromes, haemoglobin and haematin (these latter two being Fe(II) and Fe(III) complexes of proto-porphyrin respectively). The ability of other metals such as chromium and zinc to degrade DDT in vitro or in enzymic reactions is also discussed (in Stotter (1976) but without reference to porphyrins containing these metals. Ohisa et al (1980) refers to the dehalogenation of Lindane by iron-centred cytochrome P450. The interation between naturally occurring porphyrins and organohalide insecticides has been proposed as a mechanism for the degradation via dehalogenation of these insecticides by biological residues such as those in lake water (Miskus et al, (op cit), and by certain cell extracts (Ohisa et al (op cit)).

However although an effective porphyrin may degrade a wide range of organohalides little is known about optimum metal/porphyrin combinations. For example the magnesium-centred chlorophylls have little or no ability to degrade organohalides, and haematin is known to be ca twice as effective as haemin in the degradation of Lindane in identical conditions, although both have similar iron-centred structures, whilst cytochrome C, also iron-centred, does not degrade Lindane to any substantial extent.

Bieniek et al (1970) describes the dehalogenation of lindane by cyanocobalamin, both Bieniek (op cit) and Stotter (1977) refer to the dehalogenation of dieldrin (3) by cyanocobalamin. Neither of these references gives any kinetic data for the reactions of cyanocobalamin with these organohaides. Stotter (1976) and Jagnow et al (1977) refer to in vivo reactions between cyanocobalamin and a number of organohalides including chloromethanes, chloral hydrate and lindane. The degradation of DDT in cyanocobalamin-rich sewage sludge has been observed (Stotter op cit). Little work has been carried out however to identify the corrins which are most effective in the dehalogenation of organoholides, or optimum conditions under which dehalogenation may take place.

By virtue of their being naturally occurring and hence potentially cheap, porphyrins and corrins are attractive compounds for use in the degradation of organohalide pollutants.

It is an object of the invention to prepare and investigate novel metal-porphyrin and metal-corrin complexes. It is a further object of the invention to provide a novel method using novel or known metal-porphyrin, metal-corrin, and metal phthalocyanine complexes to dehalogenate organohalogen compounds.

According to the invention there are provided novel metal-porphyrin complexes, being complexes of an ion of a metal selected from osmium, ruthenium or from Group 5,6,7,9,10,11 or 12 of the periodic table with a porphyrin selected from protoporphyrin, haematoporphyrin, uroporphyrin or coproporphyrin or acid derivatives thereof in which the metal ion may be additionally complexed with a ligand, provided that if the complex is a cobalt portoporphyrin complex, the cobalt is additionally complexed with a ligand.

Further the invention also provides novel complexes of iron (II) or (III) or a Group 2 metal with haematoporphyrin, uroporphyrin or coproporphyrin or acid derivatives thereof, in which the iron may be additionally complexed with a ligand.

The formulae of the protoporphyrin, haematoporphyrin, uroporphyrin and coproporphyrin rings are shown as formulae 4A, 4B, 4C, 4D above.

The term "acid derivatives" herein is intended to include complexes in which one or more of the COOH groups on the porphyrin ring are replaced by $COONR_1R_2$ groups where $R_1$ and $R_2$ are independently alkyl or hydrogen, or salts of the COOH group with a counter cation.

The novel porphyrin complexes of this invention may for example be prepared by the following methods.

The porphyrin complexes of this aspect of the invention may be prepared by incubating together in aqueous solution the porphyrin and the metal ion, preferably in a equimolar ratio, and with an equimolar amount of the ligand if this is desired. For coproporphyrin, uroporphyrin and haematoporphyrin a solution pH of 9 (Tris/HCl buffer) and a chloride counter anion is suitable, but for protoporphyrin a solution pH of 5.5 (100 m M sodium acetate) appears to be necessary. It has been reported that protoporphyrin is hydrated to form haematoporphyrin in aqueous mineral acid solutions, so it is possible that when the reaction conditions described above for use with protoporphyrin are used the metal ion complexes with the haematoporphyrin. In the alkaline (pH 9) and acid (pH 5.5) conditions referred to above, the carboxylic acid groups on the porphyrin substitution positions may be ionized so that the complex may be present in solution as a carboxylate anion or as the free acid.

For preparation of the novel porphyrin complexes of the invention by the methods above suitable conditions are 37° C., preferably in the dark. The concentration of porphyrin, metal and ligand (if used), do not appear to be critical, but a convenient concentration is about 0.02M each. Under these conditions useful amounts of the complex are formed in about 30 minutes. The complex may then be isolated from solution using conventional methods, or may be stored in solution, preferably in the dark.

In another method of preparation, the porphyrin complex may be prepared by a microbiological process, i.e. by culturing a suitable micro-organism which produces or secretes the complex or a precursor and then harvesting these from the culture medium using known harvesting methods. The use of certain enzyme catalysts may be advantageous, for example cobalt porphyrin synthetase has been shown to catalyse the insertion of cobalt ions into porphyrins.

The invention also provides a method for dehalogenation of a halogenated organic compound, which includes the step of causing the halogenated organic compound to react with a reducing agent in the presence of either;

(i) a complex of an ion of a metal selected from osmium, ruthenium or from Group 5, 6, 7, 9 or 10 of the periodic table with a porphyrin selected from protoporphyrin, haematoporphyrin, uroporphyrin or coproporphyrin, or acid derivatives thereof, in which the metal ion may be additionally complexed with a ligand, or:

(ii) a complex of iron (II) or (III) or a Group 2 metal with a porphyrin selected from haematoporphyrin, uroporphyrin or coproporphyrin, or acid derivatives thereof, in which the iron or Group 2 metal may be additionally complexed with a ligand, or:

(iii) a complex of a corrin containing a metal centred ring system, other than cyanocobalamin.

(iv) a complex of a ion of a metal selected from Group 2, 5, 6, 8, 9 or 10 of the periodic table with a phthalocyanine.

Preferred porphyrin complexes for use in the method of the invention are those of the ions of magnesium, cobalt, nickel, molybdenum, iron and variadium. Other suitable but less preferred ions are calcium, borium, strontium, chromium, copper, manganese and zinc.

Generally complexes of haematoporphyrin are preferred, especially with cobalt (II), iron (II) and (III), magnesium, molybdenum (III), nickel (II) and vanadium (V).

The ligands with which the metal may be additionally complexed are preferably inorganic ligands, especially $CN^-$, $ClO_4^-$, $SCN^-$, $S_2O_3^{2-}$, $SO_3^{2-}$, $Cl^-$, $H_2O$, $NO_2^-$, $NO_3^-$.

Generally option (iii) is preferred, especially the use of complexes of corrins having a formula 5I:

(5I)

using the abbreviated general formula of the corrin ring. H being the metal atom or ion, A and B being the same or different coordinating ligands, and a and b each being 0 or 1.

A preferred isomeric form for the corrin ring in 5I is that found in structures 5A and 5B. The corrin ring in 5I preferably has substituents on the ring which enhance the solubility of the complex in water or enhance its ability to be bound to a solid substrate. Preferably there are up to 8 substituents independently selected from carboxylic acid-, hydroxyl-, or amide- terminated substituents or —$OCH_3$ or —$OC_2H_5$, in one or more of the 2, 3, 7, 8, 12, 13, 17 or 18 ring positions. Preferably carboxylic acid- and amide- terminated substituents have a formula $(CH_2)_n$ COX where n is 0-3 and X is respectively OH; $NR_1R_2$ where $R_1$ and $R_2$ are independently H, $C_{1-10}$ alkyl or $C_{1-10}$ hydroxy-substituted alkyl e.g. $(CH_2)_m CHOH(C_pH_{2p+1})$ where m and p are independently 1-5. Hydroxyl terminated substituents preferably have a formula $(CH_2)_r OH$ where r is 1-5.

Other substitution positions on the 5I ring if occupied by other than hydrogen are preferably occupied by substituents which do not interfere by sterically hindering the approach of the organohalogen molecule to the metal M or do by causing a deleterious electron shift in the complex. Suitable substituents on these other positions include small (e.g. $_{1-8}$) alkyl groups especially methyl, amino, cyano or ester groups, or monocyclic substituents such as in 5C. The method may also work but less satisfactorily when these other positions are occupied by larger organic residues such as the ribazole group present in dicyanocobalamin, but these may cause some interference.

The corrin ring system in complexes 5I may conveniently be, or be derived from, known corrin ring systems such as those in 5A–5H above. For example ester, amide and cyano substituents in 5A–5H may be hydrolysed to form carboxylic acid groups, which may then be converted to amide groups if desired by known methods. Additionally or alternately substituents such as the ribazole side chain of cyanocobalamin may be removed e.g. by hydrolysis of the phosphate ester link to yield cobinamide.

Preferred metals M in these corrin complexes are those of Group 2, 5, 6, 7, 8, 9, 10, 11 or 12 of the periodic table, but especially cobalt, nickel, molybdenum, iron and magnesium, particularly cobalt. In many cases corrin complexes of formula 5I in which M is other than cobalt may be prepared from known cobalt-corrin complex precursors such as those described above by reaction of a solution of the cobalt corrin complex with a chelating ligand which has a stronger affinity for cobalt than the corrin residue, such as EDTA, preferably to form an insoluble cobalt-chelating ligand complex which may easily be separated. This leaves a vacant co-ordination site in the centre of the corrin ring into which a metal ion M may be inserted by incubating the corrin with a solution of the metal ion in a manner similar to that used for the porphyrin complexes above. Suitable conditions are reaction of the precursor with an equimolar amount of the chelating ligand in aqueous solution.

Preferred ligands A and B are inorganic ligands such as $ClO_4^-$, $SCN^-$, $SO_3^-$, $S_2O_3^{2-}$, $H_2O$ and in particular $CN^-$, $Cl^-$ or $OH^-$. As many corrin complexes are known with a $Co(CN)_2$ centre it is convenient to prepare cobalt corrin complexes in which A and B are other than CN starting from a $Co(CN)_2$ centred complex precursor by incubation of the precursor with an equimolar amount of the ligand in aqueous solution.

In formula 5I, (a+b) is preferably 2 if M is cobalt II or III, and 0 if M is Ni II.

Preferred corrin complexes of formula 5I are the products of hydrolysis of cyanocobalamin (5A) or Neovitamin B12, e.g. on hydrolysis with an aqueous acid (e.g. HCl) or alkali (e.g. NaOH) on heating.

Particularly preferred corrin-cobalt complexes of formula 5I are those of formula 5J:

(5J)

in which $R^1$ is selected from $NH_2$ and OH, $R^2$ is selected from H, $CH_2CH_2COOH$ and $CH_2CH_2CONH_2$, $R^3$ is selected from H, $CH_2CH_2COOH$ and $CH_2CH_2CONH_2$, and $R^4$ is selected from $NHCH_2CH(OH)CH_3$, OH and $NH_2$.

Particularly preferred cobalt-corrin complexes of formula 5J are:

Cyanocobalamin- $SCN^-$ or $S_2O_3^{2-}$ complexes, i.e. analogues of dicyanocobalamin having A=CN and B=$SCN^-$ or $S_2O_3^{2-}$;

Cobinamide (5Bi), Neocobinamide (5Bii), Cobyric acid (5Biii), Neocobyric acid (5Biv), Cobyrinic acid (i.e. 5Bv having $R^1=R^4=OH$, $R^2=H$ $R^3=CH_2CH_2COOH$) and Neocobyrinic acid (i.e. 5Bvi having $R^1=R^4=OH$, $R^2=CH_2CH_2COOH$ $R^3=H$), i.e. having A=B=CN and a and b being 1;

and analogues of Cobinamide, Neocobinamide, Cobyric acid, Neocobyric acid, Cobyrinic acid and Neocobyrinic acid in which the $Co(CN)_2$ centre is replaced by a CoAB centre in which A and B are selected from inorganic ligands other than $CN^-$, especially $Cl^-$ and $OH^-$.

A preferred phthalocyanine for use in this method is cobalt (II) phthalocyanine, which is a known and commercially available compound.

The method of the invention is preferably carried out in an aqueous medium, e.g. in aqueous solution. When porphyrin complexes are used, pH does not appear to be too critical and a range of acid and alkaline pH can be used. Corrin complexes appear to be rather more pH dependent. In both cases a convenient pH is about pH 9.

Similarly the method is found to work over a range of temperatures, and the rate of dehalogenation generally increases with increasing temperature. Conveniently ambient temperature (ca 20° C.) may be used, and an upper optimum practical limit appears to be ca 80° C. In some cases illumination of the medium may be beneficial.

As the porphyrin, corrin and phthalocyanine complexes used in the method of the invention may in some cases have one or more functional substituents such as amine, amide, hydroxy, azo and acid groups and may in some cases have a complex stereochemistry, they may exist in a number of ionised or protonated forms depending upon the pH etc of the medium in which they are contained, and may also exist in a number of complexed forms or in an ionised form combined with a counter-ion e.g. Cl. The method of the invention includes all such forms of the complex, and all stereoisomeric forms thereof.

It is essential that the medium in which the reaction of the method takes place contains a reducing agent. These may be inorganic reducing agents such as borohydride, dithionite, sulphite, phosphite, hypo phosphite, sulphide etc. Organic reducing agents such as dithioerythreitol, dithiothreitol, mercaptosugars etc may also be used. Many such chemical reducing agents may be used and will be well known to those skilled in the art. Additionally or alternatively microorganisms which create a reducing environment or are capable of carrying out reduction may also be employed as a reducing agent, and included among these are known anaerobic microorganisms such as those which are found in soil.

The method of the invention is found to work over a wide range of concentrations of the complex, the organohalogen compound and the reducing agent. For quantitative dehalogenation of the organohalogen it is important that the medium contains at least one molar equivalent of the reducing agent per atom of halogen to be removed. Generally the complex is not used up in the method, but appears to function essentially as a catalyst assisting transfer of electrons from the reducing agent to the organohalogen compound. The ratio of complex to organohalide does not therefore appear to be critical.

In many cases the kinetics of the reaction between the complex and the halogenated organic compound shows first order kinetics, and hence the rate at which dehalogenation occurs depends upon the relative concentrations of the complex and the compound. These may be varied between wide limits and will depend upon the environment or medium in which the reaction occurs. For example the method may be used at organohalide concentrations down to ppm level as experienced in many pollution situations, and experiments have shown the method to be effective at $1 \times 10^{-5}$ M concentrations of organohalide.

The presence of other chemicals in the medium does not in many cases interfere with the method of the invention but in the case of the corrin complexes, excess cyanide in the medium may be detrimental. This cyanide may therefore be removed using known methods.

The method of the invention is suitable for dehalogenation of a wide range of halogenated organic compounds, wherein the halogen(s) may be chlorine, bromine or iodine. In general the method is more effective at dehalogenating compounds in which the halogen atom is attached to an aliphatic carbon atom than those in which the halogen is attached directly to an aromatic ring. With this reservation the compounds may for example be alkyl halides, alkenyl halides, haloalkanes or alkenes, halogenated nitrile or nitro compounds, arylalkyl or aryl-alkenyl halides, halo-ethers, or other halogenated poly-cyclic alkphatic or aromatic compounds etc.

The method is particularly attractive for the degradation by dehalogenation of halogenated organic compounds which are considered to be environmental pollutants, for example DDT, Lidane, dieldrin, hexachloro-butadiene (considered a priority pollutants by the European Economic Community). It is possible that in some circumstances the method may be used to degrade the pollutants dioxin. Other organohalogen compounds for which the method may be used will be apparent to those skilled in the art.

In many cases the method of the invention may dehalogenate these compounds to form products which are considered to be environmentally acceptable or which may be further degraded by other processes. For example the method of the invention may be used to cause an initial didechlorination of Lindane to tetrachlorocyclohexene, followed by a further dechlorination to monochloro-benzene.

In an industrial environment, the method may for example be applied by simply mixing an appropriate quantity of a metal-porphyrin, -corrin or -phthalocyanine complex with an industrial waste solution containing the undesirable organohalide, ensuring that the solution is reducing, adjusting the pH and leaving the mixture to stand for a suitable length of time, during which the quantity of the organohalide may be monitored. Other methods of treating such industrial wastes, or polluted rivers, lakes or ground etc will be apparent to those skilled in the field.

In a preferred way of perforating the dehalogenation method of the invention, the complex is immobilised on an insoluble substrate and a solution containing the halogenated organic compound is brought into contact with the immobilised complex. To ensure that a reducing agent is present the solution may contain a reducing agent or the substrate may have a reducing agent bonded or absorbed onto it.

This way of perforating the method offers the advantage that the method may be made continuous or semi-continuous, i.e. a solution to be dehalogenation (e.g. an industrial or agricultural effluent) may be passed through a bed containing a complex immobilised on a substrate, and the method need only be discontinued for regeneration of the bed. The flow rate to achieve a suitable residence time for the solution to be dehalogenated will of course depend upon the nature of the compound to be dehalogenated, the concentration etc, but experimentation of a relatively straightforward nature can determine these parameters.

The substrate may be any insoluble material, preferably otherwise inert to the solution, onto which the complex can be immobilised. To ensure that the complex is firmly immobilised onto the substrate it is preferred that the complex is chemically bound to the substrate by means of interaction between functional groups on the porphyrin, corrin or phthalocyanine ring and appropriate functional groups on the substrate. In view of the fact that the porphyrin complexes and preferred corrin complexes have carboxylate (COOH) and amide (CONH$_2$) functional substituents on their rings respectively, preferred substrates are materials which have functional groups which are capable of combining with these on their surface. For example amine (NH$_2$) and amide groups on the substrate may react with carboxylate groups on the complex, and carboxylate groups on the substrate may react with amine or amide groups on the complex, to form chemical bonds.

Many suitable substrates having such functional groups are known in particular the substrates commonly used for affinity chromatography. For example derivatised polysaccharides such as celluloses, agarose, dextrose and dextran, polyacrylamides and copolymers of these materials such as polyacrylamide-agarose gels, which may be either cross linked or non-cross linked. Alternatively derivativised inorganic oxides such as silica, alumina, titania or zirconia, or glass beads may be used. Polymeric materials such as polystyrene beads or ion-exchange resins may also be used.

Preferred substrates are derivativised forms of the known polysaccharide sepharose, particularly AH - Sepharose and CH - sepharose having respectively amino and carboxylate functional groups on their surface.

When AH - and CH - sepharoses are used to immobilise the porphyrins and preferred corrins in this way, the reaction scheme may be as below:

(where n is 0, 1 or 2)

The complex may be bound directly to the substrate by standard methods, e.g. the use of a carbodiimide coupling agent. It is preferred to bind the porphyrin or corrin first to the substrate and then to add the metal ion. Binding of the porphyrin or corrin to the substrate may also use standard methods, e.g. the use of a carbodiimide, but a preferred method for binding the porphyrin and preferred corrin complexes to a substrate which consists of a derivativised polysaccharide such as AH - or CH - Sepharose is to prepare a suspension of the substrate in a solution containing the appropriate porphyrin or corrin at pH 7 then rapidly adjusting the pH to 12 followed by a rapid adjustment of the pH to 2, then finally rapidly adjusting the pH back to 7. The substrate plus immobilised porphyrin or corrin may then be filtered off, washed, and then exposed to a solution containing metal ions, to form the immobilised complex.

When the immobilised complex is prepared in this way it is preferred to use a ratio of porphyrin or corrin in this way it is which the amount of porphyrin or corrin is in excess of that required to occupy all the available binding sites on the substrate so as to reduce any subsequent problem caused by the organohalogen compound binding to the substrate. It is also preferred to use an excess of the metal ion to ensure that as far as possible all the porphyrin or corrin rings contain a complexed metal ion.

According to a further aspect of the invention there is provided a water-insoluble substrate, having immobilised thereupon a porphyrin, corrin or phthalocyanine complex as defined above for use in the method for dehalogenation of a halogenated organic compound.

Suitable and preferred forms of such a substrate and immobilised complex are as indicated above. Such materials may be supplied separately for use in the method of the invention as discussed above, or for example contained in a cartridge through which an effluent solution to be dehalogenated may be passed.

In most cases no regeneration of the porphyrin, corrin or phthalocyanine complex appears to be necessary after the complex has been used for dehalogenation, but if the complex begins to lose its activity then exposure to a reducing agent such as that used in the dehalogenation process results in regeneration.

In a further way of carrying out the dehalogenation method of the invention, a complex of the porphyrin, corrin, or phthalocyanine either in a free form or immobilised on an immobilised substrate may be mixed with a suitable quantity of a reducing agent prior to use. Such a mixture may subsequently to introduced into an environment containing a halogenated organic compound to be dehalogenated, for example used containers for these compounds prior to disposal.

As mentioned above, the method of the invention is preferably carried out with the halogenated organic compound present in an aqueous solution. However the method may readily applied to the dehalogenation of halogenated organic compounds dispersed or suspended in an aqueous medium, or when contained in a solid or in a gas such as contaminated air. For example to treat solids, the solid may be suspended or dissolved in an aqueous medium so that the organohalogen compound partitions into the aqueous phase, where it may be dehalogenated using the method of the invention.

To treat gases, the gas may for example be bubbled through an aqueous medium containing the porphyrin, corrin or phthalocyanine complex and the reducing agent. In a preferred way of treating gases, the gas is passed through a column packed with a bed of a substrate having immobilised thereupon a porphyrin, corrin or phthalocyanine complex as described above, and a current of an aqueous medium containing a dissolved reducing agent is also passed through the bed. In both cases the organohalogen partitions between the gas and liquid phases and is dehalogenated in the liquid phase.

The invention also provides an apparatus for dehalogenation of a halogenated organic compound using the method of the invention. Preferably the apparatus uses a substrate having immobilised thereon a complex as described above and incorporates a bed of such a substrate plus complex contained within a body and being capable of having a liquid or gas containing the halogenated organic compound passed through. Such an apparatus may incorporate a replaceable cartridge containing the bed, in a construction similar to a conventional water softener or gas scrubber apparatus.

Non-limiting examples illustrating the invention will now be described, with reference to FIGS. 1 and 2 which show apparatus for dehalogenation of halogenated organic compounds according to the invention.

Abbreviations: The abbreviation "Me" is used for $CH_3$ herein

1. Preparation of porphyrin/metal ion complexes

Porphyrins (15 µg) containing no metal ions (protoporphyrins, coproporphyrin, uroporphyrin and hematoporphyrin), were dissolved in 100 mM Tris/HCl buffer (150 µl), pH 9.0, prior to incubation with equimolar solutions of a range of metal ions (present as the chloride) at 37° C. for 30 min in the dark.

A further series of complexes was prepared using protoporphyrin under conditions identical to those described above except that 100 mM sodium acetate buffer at pH 5.5 was used instead of the Tris/HCl.

1A Complexing of metal ion with ligands

Samples (15 µg) of either commercially obtained cobalt containing protoporphyrin were dissolved in 100 mM Tris/HCl buffer (150 µl), pH 9.0, prior to incubation with equimolar solutions of a variety of ligands at 37° C. for 30 min in the dark. Samples (10 µl) of the porphyrin/ligand complex were removed and assayed for the ability to dehalogenate Lindane. The absorbance spectrum of each sample was determined between 250 and 700 nm in a recording spectrophotometer (Shimadzu Model UV 240, V. A. Howe Ltd, London).

1B Dehalogenation of Lindane

Lindane dehalogenation was assayed in the following reaction mixture: 1 ml 100 mM Tris HCl buffer, pH 9.0, containing 5 mM dithiothreitol (DTT) and 10 mg/1 Lindane. The reaction was initiated by the addition of 10 µl of a sample of a solution of a complex as prepared in 1 or 2 above, and the reaction mixture was purged with nitrogen prior to incubation at 37° C. for 30 minutes. The reaction mixture was extracted with 2 ml hexane: diethyl ether (85:15, v:v) and 0.5 µl of this extract was analysed by electron capture GLC. The chromatograph was equipped with a 1.5 m×4 mm silanised glass column, packed with 3% SE30 on a 100/120 mesh Supelcoport with notrogen (40 ml/min) as the carrier gas. The injector and detector were maintained at 250° C., whilst the column oven was maintained at 190° C.

In order to assess the kinetics of dehalogenation the following reaction mixture was used: 10 ml Tris HCl buffer, pH 9.0, containing 5 mM DTT and 10 mg/1 Lindane. The reaction mixture was equilibrated at 37° C. prior to the addition of 100 µl of a sample of the complex solution prepared in 1 or 2 above, and then purged with nitrogen and sealed with a butyl rubber septum and incubated at 37° C. At 5 minute intervals, a hypodermic syringe was used to withdraw 0.5 ml samples, which were extracted with 1 ml hexane:diethyl ether (85:15 v:v), and 0.5 µl of this extract was analysed by GLC as described above.

1C Results

The results are expressed in Table 1, 2 and 3 below.

In Table 1, the various metal/porphyrin complexes without ligands which were prepared are listed together with an indicator of their relative ability to dehalogenate Lindane.

In Table 2, the effect of complexing the cobalt atom in a cobalt protoporphyrin complex with additional ligands is shown.

Table 3 shows comparative data for known metal/porphyrin complexes, for uncomplexed porphyrins and for the two known compounds cobalt phthalocyanine and cobalt protoporphyrin. In Table 3 the identity of the metal centre is indicated.

The results presented in Tables 1 and 2 demonstrate that metal/porphyrin complexes may be prepared which are effective at dehalogenating Lindane. Table 3 shows clearly that many metal/porphyrin complexes, and porphyrins without metal centres, are very ineffective in comparison with the specific complexes identified by the invention.

TABLE 1

Dehalogenation of Lindane by porphyrin/metal ion complexes

| Metal Ion | Proto-Porphyrin pH 5.5 | Proto-Porphyrin pH 9.0 | Urop porphyrin pH 9.0 | Copro-porphyrin pH 9.0 | Haemato-porphyrin pH 9.0 |
|---|---|---|---|---|---|
| None | 0 | 0 | 0 | 0 | 0 |
| Cobalt (II) | 320 | 0 | 160 | 280 | 350 |
| Copper (II) | 0 | 0 | 0 | 0 | 0 |
| Iron (II) | 240 | 0 | 56 | 110 | 250 |
| Iron (III) | 250 | 0 | 110 | 0 | 280 |
| Magnesium (II) | 350 | 0 | 140 | 300 | 350 |
| Manganese (II) | 0 | 0 | 0 | 0 | 0 |
| Molybdenum (III) | 260 | 0 | 120 | 240 | 250 |
| Nickel (II) | 220 | 0 | 130 | 210 | 200 |
| Vanadium (V) | 20 | 0 | 24 | 16 | 30 |
| Zinc (II) | 0 | 0 | 0 | 0 | 0 |

Results expressed as nmole Lindane removed/min/mg porphyrin Porphyrins and metal ions were preincubated together for 30 minutes at the pH shown in the dark prior to assay.

TABLE 2

Effect of Ligands on Lindane dehalogenation

| Ligand | Co-Protoporphyrin |
|---|---|
| None | 1300 |
| Cyanide | 1250 |
| Perchlorate | 1300 |
| Thiocyanate | 1300 |
| Thiosulphate | 1280 |
| Sulphite | 1250 |

Results expressed as nmole Lindane dehalogenated/min/mg porphyrin. All incubations carried out in the dark at 37° C.

TABLE 3

Dehalogenation of Lindane by a variety of porphyrins and analogues

| Porphyrin | M | Activity |
|---|---|---|
| Bacteriochlorophyll a (dark) | Mg | 0 |
| Chlorophyll a (dark) | Mg | 0 |
| Chlorophyll b (dark) | Mg | 0 |
| Bacteriochlorophyll a (light) | Mg | 0 |
| Chlorophyll a (light) | Mg | 0.1 |
| Chlorophyll b (light) | Mg | 0 |
| Cytochrome c | Fe | 0 |
| Haemocyanin | Cu | 0 |
| Haemoglobin | Fe (II) | 10 |
| Haemin | Fe (III) | 380 |
| Haematin | Fe (III) | 710 |
| Uroporphyrin | — | 0 |
| Coproporphyrin | — | 0 |
| Protoporphyrin | — | 0 |
| Co Phthalocyanine | Co | 560 |

TABLE 3-continued

Dehalogenation of Lindane by a variety of porphyrins and analogues

| Porphyrin | M | Activity |
|---|---|---|
| Cu Phthalocyanine | Cu | 0 |
| Co Protoporphyrin | Co | 1300 |

Results are expressed as nmole lindane dehalogenated per minute per mg of porphyrin. All incubations were at 37° C. in dark unless indicated otherwise.

2. Dehalogenation using Corrin Complexes

2A Complexing of corrin with ligands

Samples (15 μg) of commercially obtained cyanocobalamin were dissolved in 100 mM Tris/HCl buffer (150 μl), pH 9.0, prior to incubation with equimolar solutions of a variety of ligands at 37° C. for 30 min in the dark. Samples (10 μl) of the corrin/ligand complex were removed and assayed for the ability to dehalogenate Lindane. The absorbance spectrum of each sample was determined between 250 and 700 nm in a recording spectrophotometer (Shimadzu Model UV 240, V. A. Howe Ltd, London).

2B Removal of Cyanide Ligands from Cobinamide

Cobinamide (5Bi, having two CN ligands complexed to its central cobalt III ion) (10 mg) was dissolved in water (10 ml) prior to addition of 0.1M HCl to pH 2.0. The absorbance spectrum of the sample before and after acidification was determined between 250 and 700 nm in a recording spectrophotometer. The acidified sample was freeze-dried overnight and subsequently redissolved in 100 mM Tris/HCl buffer (10 ml), pH 9.0, and the pH adjusted to 9.0 by the addition of 0.01M NaOH. The absorbance spectrum of the sample was then redetermined. Samples (10 μl) were diluted in 100 mM Tris/HCl buffer (90 ul), pH 9.0, and 10 ul of this diluted material was assayed for the ability to dehalogenate lindane.

2C Deamination of Cobalamin

Cobalamin (5A, 80 mg) was dissolved in 3M sodium hydroxide (20 ml) and incubated at 80° C. for 72 hr, prior to gel filtration using Fractogel TSK-40 (column dimensions 2×50 cm) equilibrated in water. The corrin fraction was eluted using water pumped at a flow rate of 30 ml/hr. Analysis of the corrin fraction by mass spectroscopy indicated the loss of both the ribazole moiety and the amino groups in the amide substituents around the corrin ring, leading to a cobyrinic acid or an isomer thereof.

2D Dehalogenation of Lindane

Lindane dehalogenation was assayed in the following reaction mixture: 1 ml 100 mM Tris HCl buffer, pH 9.0, containing 5 mM dithiothreitol and 10 mg/1 Lindane. The reaction was initiated by the addition of 10 μl of a sample of a solution of a complex as prepared in 2A above, and the reaction mixture was purged with nitrogen prior to incubation at 37° C. for 30 minutes. The reaction mixture was extracted with 2 ml hexane:diethyl ether (85:15 v:v) and 0.5 μl of this extract was analysed by electron glc. The chromatograph wa equipped with a 1.5 m×4 mm silanised glass column packed with 3% SE30 on a 100/120 mesh Supelcoport with nitrogen (40 ml/min) as the carrier gas. The injector and detector were maintained at 250° C., whist the column oven was maintained at 190° C.

In order to assess the kinetics of dehalogenation the following reaction mixture was used: 10 ml 100 mM Tris HCl buffer, pH 9.0, containing 5 mM DTT and 10 mg/1 Lindane. The reaction mixture was equilibrated at 37° C. prior to the addition of 100 μl of a solution of the corrin complex (1 μg/10 μL). The reaction vessel was purged with nitrogen then sealed with a butyl rubber septum and incubated at 37° C. At 5 minute intervals, a hypodermic syringe was used to withdraw 0.5 ml samples, which were extracted with 1 ml hexane:diethyl ether (85:15 v:v), and 0.5 μl of this extract was analysed by GLC as described above.

Results

The various cyanocobalamin - ligand comlexes which were prepared, together with the rate at which they dehalogenated lindane (nmole lindane $min^{-1}$ $mg^{-1}$ complex) at 37° C. in the dark, are listed below in table 4. The equivalent results for cyanocobalamin and adenosylcobalamin are also given as a comparison.

TABLE 4

| Corrin | Rate of Dehalogenation |
|---|---|
| adenosylcobalamin | 750 |
| cyanocobalamin-sulphite complex | 760 |
| cyanocobalamin-perchlorate complex | 780 |
| cyanocobalamin | 800 |
| cyanocobalamin-thiosulphate complex | 800 |
| dicyanocobalamin | ca.800 |
| cyanocobalamin-thiocyanate complex | 820 |
| cobinamide (with two CN ligands) | 6750 |
| cobinamide (without CN ligands) | 6825 |
| cobyrinic acid (without CN ligands) | ≧6825 |

From the results presented in table 4 it is clear that corrin complexes have been identified which are substantially more effective at dehalogenating lindane than cyanocobalamin itself.

3. Immobilisation of Porphyrins and Corrins onto Substrates

3A Immobilisation of Porphyrins onto AH-Sepharose 4B Substrate

AH-Sepharose 4B (2 g) was swollen in 0.5M (20 ml), and washed with this solution (400 ml). The Sepharose was then washed in demineralised water adjusted to pH 4.5 (100 ml). Haematoporphyrin (40 mg) was dissolved in water (40 ml) and added to the Sepharose. The pH of the slurry was adjusted to pH 12 by addition of NaOH (10M) and held at this pH for 2 min. The pH was then adjusted to pH 2 by addition of HCl (6M) and held at this pH for a further 2 min. The slurry was then adjusted to pH 7 by further addition of NaOH prior to washing of the gel with distilled water.

Alternatively, haematoporphyrin was bound to the Sepharose by carbodiimide coupling. AH-Sepharose 4B (2 g) was swollen in 0.5M NaCl (20 ml), and washed with solution (400 ml). The Sepharose was then washed in demineralised water adjusted to pH 4.5 (100 ml). Haematoporphyrin (40 mg) was dissolved in water (40 ml) and added to the Sepharose. The pH of the slurry was adjusted to pH 5.0, prior to the addition of N-ethyl-N'-(3-dimethylaminopropyl) carbodiimide hydrochloride (EDC) to a final concentration of 100 mM. The slurry was stirred overnight at room temperature in the dark, prior to washing with distilled water. This ratio of haematoporphyrin to sepharose ensured an excess of porphyrin to available binding sites.

The substrate plus porphyrin was filtered off, washed, and treated with a large excess of the metal ion (1 mg/ml) in solution e.g. as the chloride, in a molar ratio ion porphyrin of 10:1. Excess unbound metal ion was removed by extensive washing in deionised water.

3B Immobilisation of cobalamin onto CH-Sepharose 4B

CH-Sepharose 4B (2 g) was swollen in 0.5M NaCl (20 ml), and washed with this solution (400 ml). The Sepharose was then washed in demineralised water adjusted to pH 4.5 (100 ml), Cobalamin (5A) (40 mg) was dissolved in water (40 ml) and added to the Sepharose. The pH of the slurry was adjusted to pH 5.0, prior to the addition of EDC to a final concentration of 100 mM. The slurry was stirred overnight at room temperature in the dark, prior to washing with distilled water. Problems were encountered in the immobilisation of cobalamin onto CH-Sepharose 4B, probably due to the presence of the carbonyl group of the amide.

3C Immobilisation of alkali-modified cobalamin onto AH-Sepharose

AH-Sepharose 4B (2 g) was swollen in 0.5M NaCl (20 ml), and washed with this solution (400 ml). The Sepharose was then washed in demineralised water adjusted to pH 4.5 (100 ml). Alkali-modified cobalamin prepared as in 2C above (40 mg) was dissolved in water (40 ml) and added to the Sepharose. The pH of the slurry was adjusted to pH 5.0, prior to the addition of EDC to a final concentration of 100 mM. The slurry was stirred overnight at room temperature in the dark, prior to washing with distilled water.

3D Immobilisation of alkali-modified cobalamin onto QAE-Sephadex A50

QAE-Sephadex A-50 (5 g) was mixed with alkali-modified cobalamin prepared as in 2C above (4 mg/ml; 100 ml) for 20 minutes, and the slurry then poured into a column and washed with distilled water (250 ml) prior to use.

3E Immobilisation of corrins onto Amberlite XAD-2

Amberlite XAD-2 (4 g) was added to a solution of cobalamin (5A) (80 mg) dissolved in 100 mM Tris/HCl, pH 7, (20 ml). The amberlite was then washed in the same buffer (200 ml). It was found that washing of the substrate plus corrin with water led to a slow leaching of the cobalamin from the Amberlite.

3F Immobilisation of modified cobalamin onto polystyrene beads

Alkali-modified cobalamin prepared as in 2C above was immobilised onto two types of polystyrene beads, differentiated by their functional groups, either hydrazide or alkylamine moieties.

Hydrazide-derivatized polystyrene beads (6 mm diameter (25) were placed in a solution of alkali-modified cobalamin (4 mg/ml in water; 10 ml), and the pH adjusted to 5.5 prior to the addition of EDC to a final concentration of 100 mM. After mixing overnight at room temperature in the dark on a bottle-roller, the beads were washed with distilled water prior to use.

Alkylamine-derivatized polystyrene beads (25) were placed in a solution of alkali-modified cobalamin (4 mg/ml in water:methanol (1:1;v:v); 10 ml), and the pH adjusted to 8.0. After mixing for 2 hours at room temperature in the dark on a bottle roller, the beads were washed with distilled water prior to use.

4. Dehalogenation Assays: Liquid Phase

4A All of the immobilised catalysts were tested for the ability to dehalogenate either lindane (γ-hexachlorocylohexane), carbon tetrachloride, trichloroethylene or dichloromethane. The immobilised catalysts were poured into a column to provide a bed volume of 5 ml, with the exception of the polystyrene beads where 25 beads were used in a column. A solution of 100 mM Tris/HCl, at a pH of either 7.0 or 9.0, containing 5 mM DTT and either 10 ppm lindane or 100 ppm of carbon tetrachloride, dichloromethane or trichloroethylene was pumped through the column at flow rates suitable to give residence times of 5, 10 and 20 minutes. Effluent from the column (1 ml) was extracted with diethyl ether/hexane (15:85, v:v; 2 ml) prior to analysis by electron-capture GLC.

4B Dehalogenation using Immobilised Porphyrins

Immobilisation of haematoporphyrin onto AH-Sepharose, either by pH shift or carbodiimide coupling, and subsequent washing in a solution of either cobalt chloride or magnesium chloride (as described in 3A), resulted in the formation of a catalyst capable of the dehalogenation of lindane (Tables 5 and 6), although dehalogenation by the column equilibrated with cobalt was more effective than that equilibrated with magnesium. The column equilibrated with cobalt was able to dehalogenate lindane at over 99% dehalogenation of a 10 ppm solution at a residence time of 10 minutes for over 76 days. After 257 days this column was still able to dehalogenate 66% of the lindane under the same conditions.

TABLE 5

| \multicolumn{3}{c}{Dehalogenation using bound Cobalt-Haematoporphyrin} |
|---|---|---|
| Days of operation | Residence time (minutes) | % Lindane dehalogenated |
| 0 | 10 | 99.6 |
| 1 | 5 | 98.4 |
| 1 | 10 | 99.5 |
| 1 | 20 | 99.8 |
| 2 | 10 | 99.5 |
| 5 | 10 | 99.5 |
| 9 | 10 | 99.3 |
| 13 | 5 | 96.8 |
| 13 | 10 | 99.4 |
| 13 | 20 | 99.6 |
| 15 | 5 | 99.4 |
| 15 | 10 | 99.6 |
| 15 | 20 | 99.7 |
| 18 | 10 | 99.4 |
| 21 | 5 | 99.3 |
| 21 | 10 | 99.5 |
| 21 | 20 | 99.8 |
| 28 | 5 | 98.8 |
| 28 | 10 | 99.3 |
| 28 | 20 | 99.5 |
| 33 | 5 | 99.5 |
| 33 | 10 | 99.7 |
| 33 | 20 | 99.9 |
| 45 | 5 | 99.2 |
| 45 | 10 | 99.6 |
| 45 | 20 | 99.4 |
| 61 | 5 | 99.5 |
| 61 | 10 | 99.5 |
| 61 | 20 | 99.3 |
| 76 | 5 | 99.0 |
| 91 | 5 | 98.5 |
| 91 | 10 | 98.8 |
| 91 | 20 | 98.8 |
| 257 | 10 | 66.2 |

TABLE 6

| Dehalogenation using bound Magnesium-Haematoporphyrin | | |
|---|---|---|
| Days of operation | Residence time (minutes) | % Lindane dehalogenated |
| 0 | 5 | 79 |
| 0 | 10 | 91 |
| 0 | 20 | 96 |
| 7 | 5 | 77 |
| 7 | 10 | 92 |
| 7 | 20 | 94 |

Using the method of 1B, 2D, 4A and 4B above it was also possible to dehalogenate carbon tetrachloride, methane being the ultimate product.

4C Dehalogenation using Immobilised Corrins

When immobilised onto AH-Sepharose, alkali-modified cobalamin (3C product) was capable of the dehalogenation of lindane. Over 99% of a 10 ppm solution of lindane could be dehalogenated by this system at a residence time in the column of 5 minutes.

When immobilised onto QAE-Sephadex, alkali-modified cobalamin (3D product) dehalogenated over 99% of a 10 ppm solution of lindane at a residence time of 5 minutes. Both carbon tetrachloride and dichloromethane were dehalogenated by this system: 99% of a 100 ppm solution of either compound could be dehalogenated at a residence time of 10 minutes. In both cases, methane was identified as an end product. No dehalogenation of trichloroethylene was observed with this system, and the presence of trichloroethylene appeared to cause a slow leaching of the alkali-modified cobalamin from the Sephadex.

When alkali-modified cobalamin was immobilised onto hydrazide-derivatized polystyrene beads (3F product) by coupling with EDC, over 99% of a 10 ppm solution of lindane was dehalogenated when the solution was delivered at a flow rate equivalent to that necessary to provide a residence time of 5 minutes for the other matrices (i.e. 60 ml/h). Carbon tetrachloride, dichloromethane and trichloroethylene were not dehalogenated by this system.

When immobilised onto alkylamine-derivatized polystyrene beads (3F product), alkali-modified cobalamin again catalysed the dehalogenation of over 99% of a 10 ppm solution of lindane when the solution was delivered at a flow rate of 60 ml/h. In addition, 99% of 100 ppm solutions of either carbon tetrachloride or dichloromethane could be dehalogenated when pumped at flow rates of 60 ml/h.

5. Gas-phase dehalogenation

In order to assess the potential of immobilised corrins to dehalogenate gaseous organohalides, alkali-modified cobalamin (2C product) immobilised onto both QAE-Sephadex and alkylamine-derivatized polystyrene beads was tested for their ability to dehalogenate dichloromethane. Air saturated with dichloromethane was pumped through a column of either QAE-Sephadex (5 ml) or alkylamine-derivatized polystyrene beads (25) to which alkali-modified cobalamin had been bound, at a flow rate of 400 ml/h. In addition, 500 mM DTT was pumped onto the column at a flow rate of 4 ml/h. The gas phase emerging from the column was bubbled through diethyl ether/hexane (15:85; v:v; 10 ml), which was periodically assayed by electron capture GLC for the presence of dichloromethane. The levels of dichloromethane passing through the columns in the absence of DTT were taken as controls.

When air saturated with dichloromethane (approx 400 ppm) was passed through the column of alkali-modified cobalamin immobilised to QAE-Sephadex, approximately 92% of the dichloromethane was dehalogenated. Similarly, when air saturated with dichloromethane was passed through the column of alkali-modified cobalamin immobilised to alkylamine-derivatized polystyrene beads, approximately 70% of the dichloromethane was dehalogenated.

6. Dehalogenation Apparatus

Figures 1, 2:
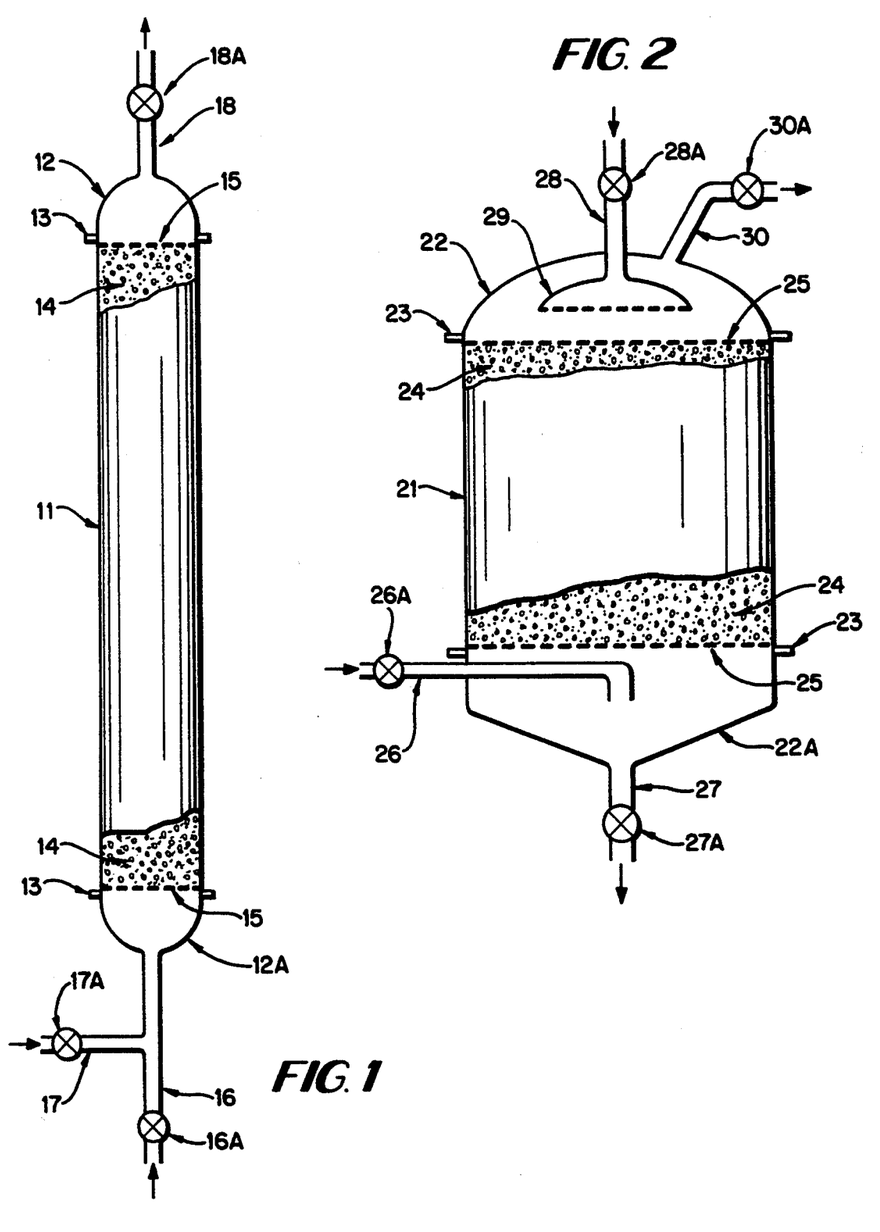

FIGS. 1 and 2 show respectively apparatus for dehalogenation of aqueous or gaseous effluent.

In apparatus comprises a body (11, 21), having at its upper end an upper closure (12, 22) and at its lower end a lower closure (12A, 22A), the seals (13, 23) between the body (11, 21) and the closures (12, 12A, 22, 22A) being releasable but watertight or airtight as appropriate. Each body (11, 21) is largely filled with polystyrene beads (14, 24) having immobilised thereon a corrin (e.g. the 3F product) retained in place in the body (11, 21) by retaining grids (15, 25).

In the lower closure (12A) are connected inlets (16), (17), through which flow may be controlled by valves (16A), (17A). The upper closure (12) is an outlet (18) flow through which may be controlled by a valve (18A).

In the closure (22A) is an inlet (26), and an outlet (27), and flow through these may be controlled by valves (26A) and (27A). In the upper closure (22) there is an inlet (28), flow through which may be controlled by valve (28A). The tube (28) communicates with a sprinkler (29) inside the closure (22). There is also an outlet (30) in the closure (20), flow through which is controlled by a valve (30A).

An aqueous effluent to be dehalogenated is passed through inlet (16). A solution of a reducing agent is passed through inlet (17), mixing with the effluent. The mixture passes up the body (11) and contacts the beads (14), upon which dehalogenation takes place. Dehalogenated effluent leaves via outlet (18).

A gaseous effluent to be dehalogenated is passed through inlet (26). At the same time a solution of a reducing agent is passed through inlet (28) so as to moisten all the beads (24) with the reducing solution. As the gaseous effluent contacts the beads (24), dehalogenation of the effluent occurs, and dehalogenated effluent leaves via outlet (30). Excess reducing agent leaves via outlet (27) and may for example be treated with the apparatus of FIG. 1 or otherwise disposed of.

The grids (15, 25) prevent escape of the beads (14, 24). The effluent from outlets (18, 30) may be monitored, and when the beads (14, 24) appear to be exhausted, the seals (13, 23) may be released and a whole new body (11, 21) put in its place, i.e. as a replaceable dehalogenation cartridge.

References

Wade R. S. & Castro C. E. J Am Chem Soc (1973) 95, 226–230.

Miskus R. P., Blair D. P. & Casida J. E. J Agr Food Chem (1965) 13, 481–483.

Zoro J. A., Hunter J. M., Eglinton G., Ware G. C., Nature (1974) 247, 235–237

Castro C. E., J Am Chem Soc (Comm) (1954), 86, 2310–2311

Stotter D. A., J-Inorg-Nucl Chem (1977) 39, 721–727

Ohisa N., Yamaguchi M., Kurihara N., Arch Microbiol (1980) 125, 221

Bieniek D., Mosa P. N., Klein W. and Korte F. (1970), Tetrahedron Lett 47, 4055–4058

Jagnow G., Haider K., Ellwart P. C., (1977), Arch-Microbiol, 115, 285

Bonnett R., Godfrey J. M., Math V. B. J Chem Soc (C) (1971) 3736–3743

Gossauer A., Heise K., Cotze H., Inhoffen H., Liebigs Ann Chem (1977) 1480–1499

Bormann D., Fischli A., Keese R., Eschenmoser A. Angew Chem Int Edn (1967) 6(10) 868–871

Holze G., Gossauer A., Helv Chim Acta (1986) 69 1567–1570

We claim:

1. A method for dehalogenation of a halogenated organic compound suspended, dispersed or dissolved in an aqueous medium, said method comprising the step of causing the halogenated compound to react with a reducing agent in the presence of a complex of a corrin containing a metal centered ring system of the formula:

where M is cobalt, nickel, molybdenum, iron or magnesium; A and B are coordinating ligands which may be the same or different; a and b are each 0 or 1; $R^1$ is selected from the group consisting of $NH_2$ and OH; $R^2$ is selected from the group consisting of H, $CH_2CH_2COOH$ and $CH_2CH_2CONH_2$; $R^3$ is selected from the group consisting of H, $CH_2CH_2COOH$ and $CH_2CH_2CONH_2$; and $R^4$ is selected from the group consisting of $NHCH_2CH(OH)CH_3$, OH and $NH_2$,
wherein the halogenated compound suspended, dispersed or dissolved in the aqueous medium is an environmental pollutant or industrial waste and the dehalogenated reaction is carried out between ambient temperature and 80° C.

2. The method according to claim 1 wherein the dehalogenation reaction is carried out at between 20° C. and 80° C.

3. The method according to claim 1 herein the dehalogenation step is carried out at about pH 9.

4. The method according to claim 1 wherein the dehalogenation step is carried out in the absence of light.

5. The method according to claim 1 wherein A and B are both $CN^-$.

6. The method according to claim 1 wherein a and b are both 0.

7. The method according to claim 1 wherein M is cobalt.

8. The method according to claim 1 wherein $R^1$ is $NH_2$, $R^2$ is H, $R^3$ is $CH_2CH_2CONH_2$, $R^4$ is $NHCH_2CH(OH)CH_3$, M is cobalt, A and B are both $CN^-$ and a and b are both 1.

9. The method according to claim 1 wherein $R^1$ is $NH_2$, $R^2$ is H, $R^3$ is $CH_2CH_2CONH_2$, $R^4$ is $NHCH_2CH(OH)CH_3$, M is cobalt, and a and b are both 0.

10. The method according to claim 1 wherein $R^1$ is $NH_2$, $R^2$ is H, $R^3$ is $CH_2CH_2CONH_2$, $R^4$ is OH, M is cobalt, and a and b are both 0.

11. A method for dehalogenation of a halogenated organic compound suspended, dispersed or dissolved in an aqueous medium, said method comprising the step of causing the halogenated compound to react with a reducing agent in the presence of a complex of a corrin containing a metal centered ring system of the formula:

where M is cobalt, nickel, molybdenum, iron or magnesium; A and B are coordinating ligands which may be the same or different; a and b are each 0 or 1; $R^1$ is selected from the group consisting of $NH_2$ and OH; $R^2$ is selected from the group consisting of H, $CH_2CH_2COOH$ and $CH_2CH_2CONH_2$; $R^3$ is selected from the group consisting of H, $CH_2CH_2COOH$ and $CH_2CH_2CONH_2$; and $R^4$ is selected from the group consisting of $NHCH_2CH(OH)CH_3$, OH and $NH_2$,
wherein the halogenated compound suspended, dispersed or dissolved in the aqueous medium is an environmental pollutant or industrial waste and the dehalogenated reaction is carried out between 20° C. and 80° C., at a pH of about 9 and in the absence of light.

12. The method according to claim 11 wherein $R^{11}$ is $NH_2$, $R^2$ is H, $R^3$ is $CH_2CH_2CONH_2$, $R^4$ is $NHCH_2CH(OH)CH_3$, M is cobalt, A and B are both $CN^-$ and a and b are both 1.

13. The method according to claim 11 wherein $R^1$ is $NH_2$, $R^2$ is H, $R^3$ is $CH_2CH_2CONH_2$, $R^4$ is $NHCH_2CH(OH)CH_3$, M is cobalt, and a and b are both 0.

14. The method according to claim 11 wherein $R^1$ is $NH_2$, $R^2$ is H, $R^3$ is $Ch_2CH_2CONH_2$, $R^4$ is OH, M is cobalt, and a and b are both 0.

15. The method according to claim 11, wherein the complex is immobilized on a water insoluble substrate.

16. The method according to claim 15 wherein the substrate is a derivatized polysaccharide, polyacrylamide or polystyrene, a derivatized inorganic oxide or an ion-exchange resin.

17. The method according to claim 15 wherein the immobilized complex is situated in a bed and the halogenated compound suspended, dispersed or dissolved in the aqueous medium is passed through the bed in the presence of reducing agent.

18. The method according to claim 15 wherein the immobilized complex is in the form of a bed, wherein the immobilized compound suspended, dispersed or dissolved in the aqueous medium is passed through the bed in the presence of reducing agent, wherein the pH of the medium is about pH 9 and the residence time in the bed is from 5 to 20 minutes.

19. The method according to claim 1 wherein the halogenated compound has the halogen to be removed attached to an aliphatic carbon atom.

20. The method according to claim 1 wherein the halogenated compound is selected from the group consisting of DDT, lindane, dieldrin, hexachloro-butadiene, carbon tetrachloride, and dichloromethane.

21. The method according to claim 15 wherein the halogenated compound is selected from the group consisting of carbon tetrachloride, dichloromethane and lindane, wherein the concentration of compound in the aqueous medium is up to 100 ppm, the reaction time is 10 minutes or less and 99% or more of the compound is dehalogenated.

22. The method according to claim 15, wherein the substrate is a sepharose and the complex is immobilized on the sepharose through amide bonds formed by reacting one or more of the carboxylic acid or carboxylic acid amide groups on the complex with amine or carboxylic acid groups on the sepharose.

23. The method according to claim 15 wherein the substrate is an alkylamine-derivatized polystyrene and the complex is immobilized on the alkylamine-derivatized polystyrene through amide bonds formed by reacting one or more of the carboxylic acid groups on the complex with the alkylamine groups on the polystyrene.

* * * * *